US011666492B2

(12) United States Patent
Tong et al.

(10) Patent No.: US 11,666,492 B2
(45) Date of Patent: Jun. 6, 2023

(54) PANT-TYPE WEARABLE ARTICLE

(71) Applicant: The Procter & Gamble Company, Cincinnati, OH (US)

(72) Inventors: Ling Tong, Beijing (CN); Koichi Morimoto, Beijing (CN); Chunmin Cheng, Beijing (CN); Albert Choy So, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 863 days.

(21) Appl. No.: 16/690,179

(22) Filed: Nov. 21, 2019

(65) Prior Publication Data
US 2020/0085645 A1    Mar. 19, 2020

Related U.S. Application Data

(63) Continuation of application No. PCT/CN2018/086678, filed on May 14, 2018, and a
(Continued)

(51) Int. Cl.
*A61F 13/49* (2006.01)
*A61F 13/496* (2006.01)

(52) U.S. Cl.
CPC .. *A61F 13/49012* (2013.01); *A61F 13/49017* (2013.01); *A61F 13/49061* (2013.01); *A61F 13/4963* (2013.01)

(58) Field of Classification Search
CPC ............ A61F 13/49061; A61F 13/4906; A61F 13/49012; A61F 13/49017; A61F 13/4963; A61F 2013/49093
See application file for complete search history.

(56) References Cited

U.S. PATENT DOCUMENTS

2012/0116343 A1*  5/2012  Yoshioka ............... A61F 13/496
                                                            604/385.29
2013/0211363 A1   8/2013  LaVon et al.
(Continued)

FOREIGN PATENT DOCUMENTS

CN      105380754        3/2016
CN      206214287 U      6/2017
(Continued)

OTHER PUBLICATIONS

International Search Report and Written Opinion, PCT/CN2018/0086678.
(Continued)

*Primary Examiner* — Susan S Su
(74) *Attorney, Agent, or Firm* — Charles R. Matson (57) ABSTRACT

Disclosed is a wearable article continuous in a longitudinal direction and a transverse direction comprising a front elastic belt region, a back elastic belt region, a crotch region, a waist opening and two leg openings; the crotch region extending longitudinally between the front elastic belt region and the back elastic belt region; the front elastic belt region having an area of A1, the crotch region having an area of A2, the back elastic belt region having an area of A3, the front elastic belt region having a front placement distance L8, and the back elastic belt region having a back placement distance L9 according to the measurements herein; wherein the total of A1, A2 and A3 is from about 1250 cm² to about 1400 cm², and having a relationship of A3>A1>A2; and wherein the ratio of L8 to L9 is no more than about 0.8.

10 Claims, 9 Drawing Sheets

Related U.S. Application Data continuation-in-part of application No. PCT/CN2017/094610, filed on Jul. 27, 2017.

(56) References Cited

U.S. PATENT DOCUMENTS

| | | | |
|---|---|---|---|
| 2015/0173973 A1 | 6/2015 | Lavon | |
| 2016/0184145 A1* | 6/2016 | Morimoto | A61F 13/496 604/385.29 |
| 2016/0206482 A1* | 7/2016 | Nishikawa | A61F 13/49406 |
| 2017/0165128 A1 | 6/2017 | Morimoto | |
| 2019/0274896 A1 | 9/2019 | Morimoto | |

FOREIGN PATENT DOCUMENTS

| | | | | |
|---|---|---|---|---|
| GB | 2474587 B | 10/2011 | | |
| JP | 2007195647 A | 8/2007 | | |
| JP | 2016530961 A | 10/2016 | | |
| WO | WO-2015068480 A1 * | 5/2015 | ....... | A61F 13/49012 |
| WO | WO2016029374 A1 | 3/2016 | | |
| WO | WO2018094676 A1 | 5/2018 | | |

OTHER PUBLICATIONS

International Search Report and Written Opinion; Application Ser. No. PCT/CN2017/094610, dated Apr. 18, 2018, 8 pages.
PCT/CN2108/086678 PCT International Search Report dated Oct. 29, 2019, 7 pages.

* cited by examiner

PANT-TYPE WEARABLE ARTICLE

CROSS REFERENCE TO RELATED APPLICATIONS

This application is a continuation, under 35 USC 120, of PCT Application No. PCT/CN2018/086678, filed on May 14, 2018, and this application is a continuation-in-part, under 35 USC 120, of PCT Application No. PCT/CN2017/094610, filed on Jul. 27, 2017, both of which are incorporated by reference herein.

FIELD OF THE INVENTION

The present invention relates to pant-type wearable articles having a particular dimensional relationship among its structural components.

BACKGROUND OF THE INVENTION

Infants and other incontinent individuals wear absorbent articles such as diapers to receive and contain urine and other body exudates. Pull-on absorbent articles, or pant-type absorbent articles, are those which are donned by inserting the wearer's legs into the leg openings and sliding the article up into position about the lower torso. Pant-type absorbent articles have become popular for use on children who are able to walk and often who are toilet training, as well as for younger children who become more active in movement such that application of taped-type absorbent articles tends to be more difficult, and also for younger babies requiring a soft fit around the waist opening and leg openings.

Pant-type articles may take various structures wherein the circumference of the waist opening and vicinity thereof is made elastic enough to facilitate the wearer or the caregiver to expand the article and insert the wearer's legs into the leg openings for wearing the article. The region of the waist circumference and vicinity thereof is often referred to as the elastic belt. One type of structure for the pant-type article is the belt-type pant having a central chassis to cover the crotch region of the wearer and a separate elastic belt defining the waist opening and leg opening, such as described in PCT Publication WO 2006/17718A. Another type of structure for the pant-type article is the uni-body pant configured such that the outer cover of the article completely covers the entirety of the garment-facing surface of the article, wherein the portion configured to stretch about the torso is considered the elastic belt region.

Whatever the structure of the pant-type article may be, pant-type articles provide no or only a very small range of size adjustment or body configuration adjustment based on the structural limitations of the article. As such, pant-type articles are typically so configured to accommodate size and configuration ranges by providing the elastic belt region very stretchable and comfortable to wear, yet with reliable fit such that sufficient protection against sagging and leakage may be provided. Further, the elastic belt region may be the portion which is most touched and observed by the wearer or the caregiver upon use, and thus its properties most associated with the quality of the article. By quality, what may be desired is an undergarment-like integral appearance and feel.

Based on the foregoing, there is a need for a wearable article providing improved fit properties over a wide range of body size ranges without compromise to comfort or ease of application. There is also a need for providing such a wearable article having improved undergarment-like integral appearance which can be economically made.

SUMMARY OF THE INVENTION

The present invention is directed to a wearable article continuous in a longitudinal direction and a transverse direction comprising a front elastic belt region, a back elastic belt region, a crotch region, a waist opening and two leg openings; the crotch region extending longitudinally between the front elastic belt region and the back elastic belt region;

the front elastic belt region having an area of A1, the crotch region having an area of A2, the back elastic belt region having an area of A3, the front elastic belt region having a front placement distance L8, and the back elastic belt region having a back placement distance L9 according to the measurements herein;

wherein the total of A1, A2 and A3 is from about 1250 $cm^2$ to about 1400 $cm^2$, and having a relationship of A3>A1>A2; and wherein the ratio of L8 to L9 is no more than about 0.8.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

DEFINITIONS

As used herein, the following terms shall have the meaning specified thereafter:

"Wearable article" refers to articles of wear which may be in the form of pants, taped diapers, incontinent briefs, feminine hygiene garments, and the like. The "wearable article" may be so configured to also absorb and contain various exudates such as urine, feces, and menses discharged from the body. The "wearable article" may serve as an outer cover adaptable to be joined with a separable disposable absorbent insert for providing absorbent and containment function, such as those disclosed in PCT publication WO 2011/087503A.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants".

"Longitudinal" refers to a direction running substantially perpendicular from a waist edge to an opposing waist edge of the article and generally parallel to the maximum linear dimension of the article.

"Transverse" refers to a direction perpendicular to the longitudinal direction.

"Proximal" and "distal" refer respectively to the position closer or farther relative to the longitudinal center of the article.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable".

"Extendibility" and "extensible" mean that the width or length of the component in a relaxed state can be extended or increased.

"Elasticated" and "elasticized" mean that a component comprises at least a portion made of elastic material.

"Elongatable material", "extensible material", or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

"Artwork" refers to a visual presentation to the naked eye, which is provided by printing or otherwise, and having a color. Printing includes various methods and apparatus well known to those skilled in the art such as lithographic, screen printing, flexographic, and gravure ink jet printing techniques.

"Color" or "Colored" as referred to herein includes any primary color except color white, i.e., black, red, blue, violet, orange, yellow, green, and indigo as well as any declination thereof or mixture thereof. The color white is defined as those colors having a L* value of at least 94, an a* value equal to 0±2, and a b* value equal to 0±2 according to the CIE L* a* b* color system.

DETAILED DESCRIPTION OF THE INVENTION

Figure 1:
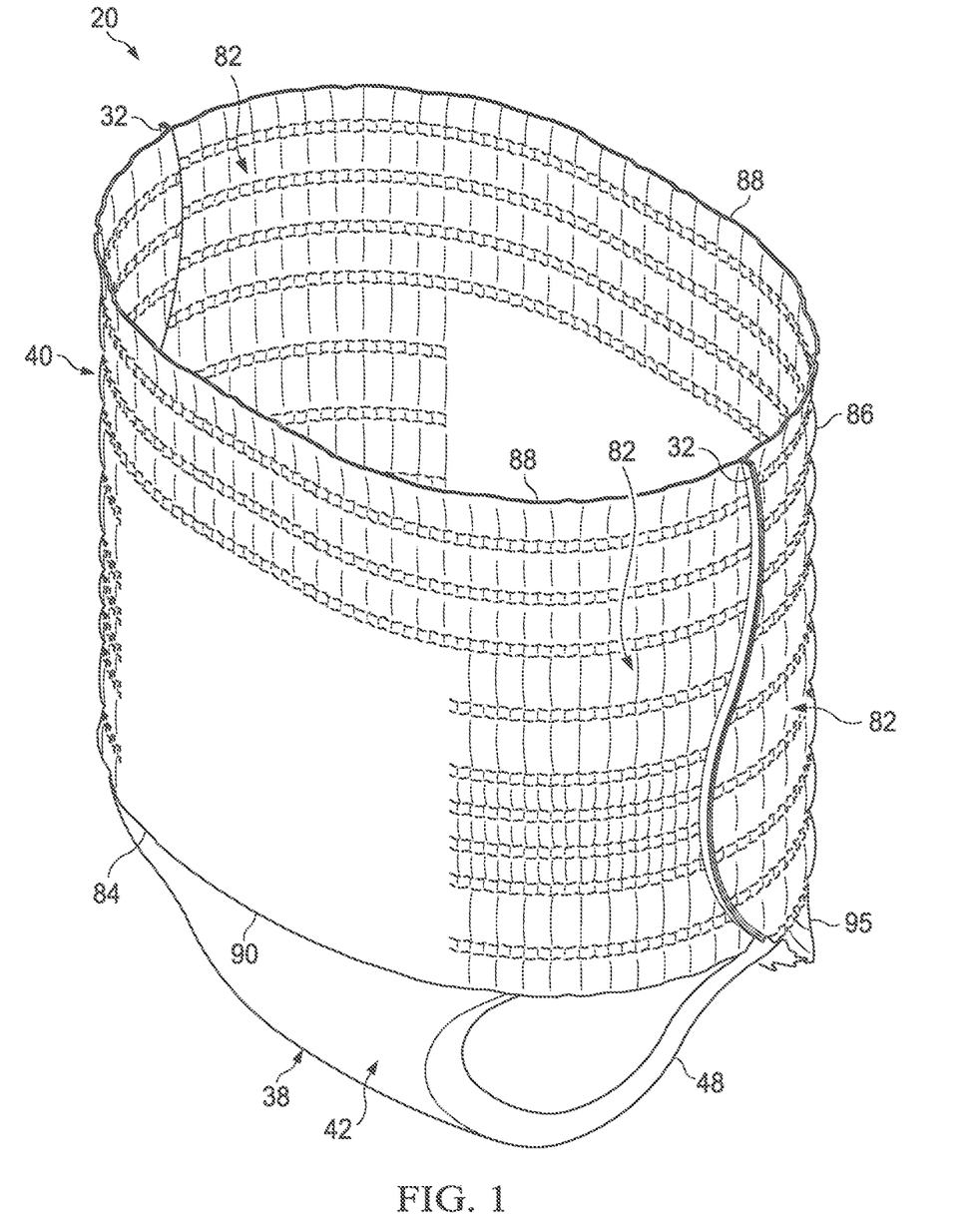
FIG. 1 is a perspective view of one embodiment of a wearable article of the present invention.
Figure 2:
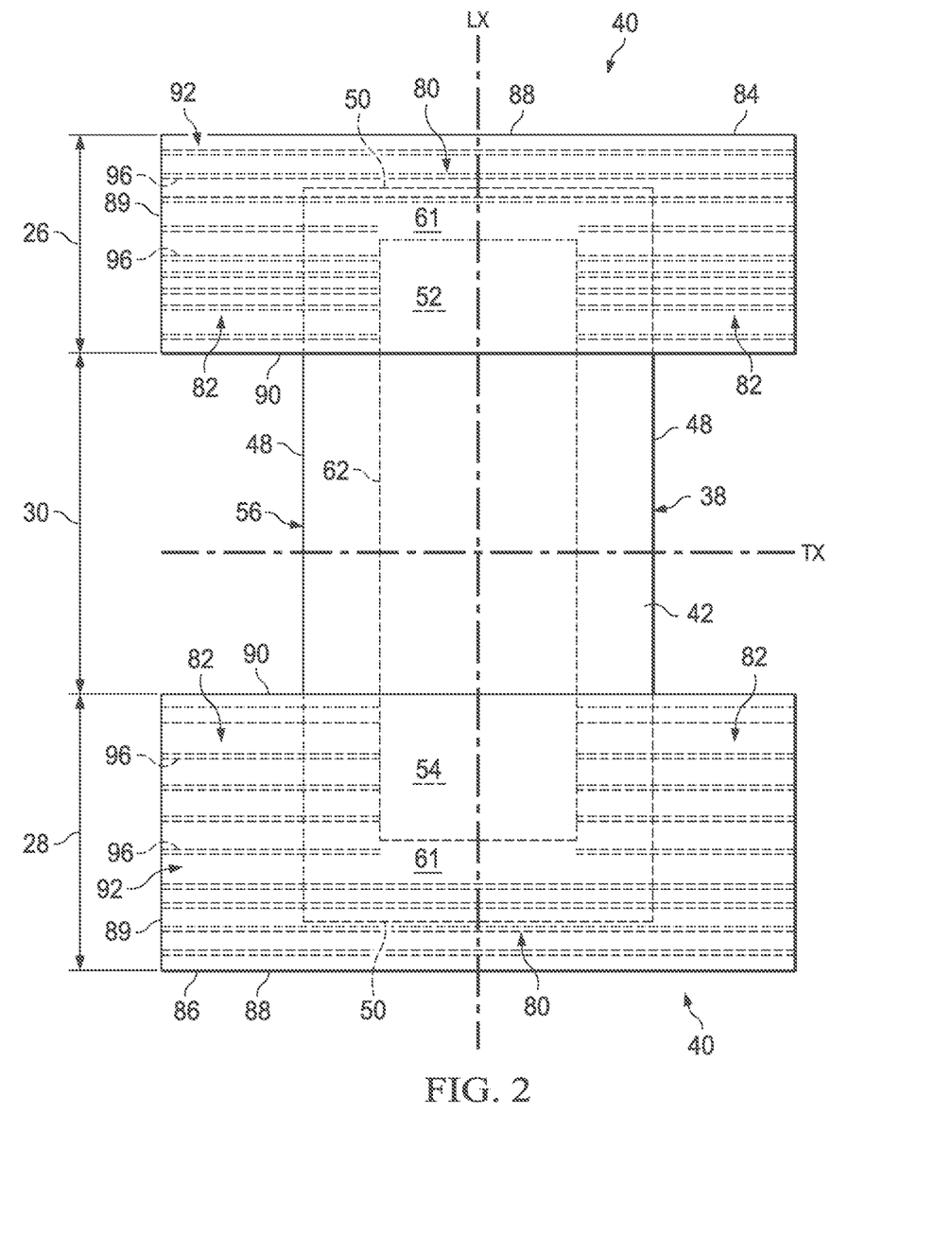
FIG. 2 is a schematic plan view of one embodiment of a wearable article of the present invention with the seams unjoined and in a flat uncontracted condition showing the garment facing surface.

FIG. 1 is a perspective view of an embodiment of the wearable article 20 of the present invention and FIG. 2 is a schematic plan view of the same article with the seams unjoined and in its flat uncontracted condition showing the garment-facing surface. The wearable article 20 has a longitudinal centerline LX which also serves as the longitudinal axis, and a transverse centerline TX which also serves as the transverse axis. The wearable article 20 has a body facing surface, a garment facing surface, a front region 26 where the front elastic belt region 84 exists, a back region 28 where the back elastic belt region 86 exists, a crotch region 30, and side seams 32 which join the front region 26 and the back region 28 to form two leg openings and a waist opening.

The wearable article 20 may be a belt-type pant as in FIGS. 1 and 2 comprising a central chassis 38 to cover the crotch region 30 of the wearer, a front belt 84 and a back belt 86 (hereinafter may be referred to as "front and back belts"), the front and back belts 84, 86 forming a discrete ring-like elastic belt 40 (hereinafter may be referred to as "waist belt") extending transversely defining the waist opening. For the belt-type pant, the discrete ring-like elastic belt 40 may also be referred to as the elastic belt region 40. For the belt-type pant as in FIGS. 1, 2, 3A and 3B, the front and back belts 84, 86 and the central chassis 38 jointly define the leg openings. The wearable article 20 may be a pant as in FIG. 3C wherein the side edges of the central chassis 38 are curved, wherein the curved circumference defines a majority of the leg opening.

The central chassis 38 may comprise a topsheet, a backsheet and an absorbent core 62 disposed between the topsheet and the backsheet, and further an outer cover layer 42 for covering the garment-facing side of the backsheet. The topsheet may be a water permeable substrate. The backsheet may be a water impermeable film. The outer cover layer 42 may be a nonwoven sheet. The central chassis 38 may contain an absorbent core 62 for absorbing and containing body exudates disposed on the central chassis 38, and an absorbent material non-existing region 61 surrounding the periphery of the absorbent core 62. The absorbent material non-existing region 61 may be made of the topsheet and/or the backsheet and/or the outer cover layer 42 and/or other parts configuring the central chassis 38. In the embodiment shown in FIG. 2, the central chassis 38 has a generally rectangular shape, left and right longitudinally extending side edges 48 (hereinafter may be referred to as "side edge") and front and back transversely extending end edges 50 (hereinafter may be referred to as "end edge"). The absorbent core 62 may exist through the entire longitudinal dimension of the crotch region and extending at least partly in the front elastic belt region 84; or at least partly in both the front and back elastic belt regions 84, 86. The central chassis 38 may have a front waist panel 52 positioned in the front region 26 of the absorbent article 20, a back waist panel 54 positioned in the back region 28, and a crotch panel 56 between the front and back waist panels 52, 54 in the crotch region 30. The center of the front belt 84 is joined to a front waist panel 52 of the central chassis 38, the center of the back belt 86 is joined to a back waist panel 54 of the central chassis 38, the front and back belts 84, 86 each having a left side panel and a right side panel 82 where the central chassis 38 does not overlap. The central chassis has a crotch panel 56 positioned between the front waist panel 52 and the back waist panel 54. The front and back belt 84, 86 may be discontinuous of each other in the longitudinal direction.

The absorbent core 62 may include an absorbent layer and an acquisition layer. The absorbent layer is the region wherein absorbent materials having a high retention capacity, such as superabsorbent polymers, are present. The absorbent layer may be substantially cellulose free. Superabsorbent polymers of the absorbent layer may be disposed between first and second layers of material immobilized by a fibrous layer of thermoplastic adhesive material. The first and second layers of materials may be nonwoven fibrous webs including synthetic fibers, such as mono-constituent fibers of PE, PET and PP, multiconstituent fibers such as side by side, core/sheath or island in the sea type fibers. Such synthetic fibers may be formed via a spunbonding process or a meltblowing process. The acquisition layer facilitates the acquisition and the distribution of body exudates and may be placed between the topsheet and the absorbent layer. The acquisition layer may include cellulosic fibers.

The absorbent layers may be disposed in plurality in the absorbent core 62. Some portions of the absorbent layers may be configured to have substantially no absorbent material to form a channel or a plurality of channels. Channels may be useful for allowing the absorbent core to bend upon swelling with fluids, such that the absorbent article conforms to the wearer's body after swelling and prevent sagging of the article. The channels may also be formed in the acquisition layer, and may be configured to at least partly match the channels of the absorbent layer in the thickness direction.

The elastic belt region 40 of the article of the present invention acts to dynamically create fitment forces and to distribute the forces dynamically generated during wear. The front and back belts 84, 86 may be joined with each other only at the side edges 89 at the seams 32 to form a wearable article having a waist opening and two leg openings. Each leg opening may be provided with elasticity around the perimeter of the leg opening. The elasticity around the leg opening may be provided by the combination of elasticity from the front belt 84, the back belt 86, and any from the central chassis 38.

The transverse width of the backsheet and the outer cover layer 42 may be the same, or may be varied (not shown). For example, the backsheet may have a shorter transverse width compared to that of the outer cover layer 42. By such configuration, the longitudinal side edges 48 of the crotch panel 56, which make part of the leg openings, may have better breathability. Further, such configuration may provide cost saving.

The front belt 84 and back belt 86 are configured to impart elasticity to the belt 40. The front belt 84 and the back belt 86 may each be formed by a laminate comprising a plurality of elastic bodies 96 running in the transverse direction, an inner sheet 94, an outer sheet 92, and an outer sheet fold over (not shown) wherein the outer sheet fold over is an extension of the outer sheet material formed by folding the outer sheet material at the distal edge 88 of the front and back belts; wherein the belt elastic bodies 96 are sandwiched between two of these sheets. The front belt 84 and the back belt 86 may each be made only by elastic bodies 96, the inner sheet 94, the outer sheet 92, and the outer sheet fold over. The belt elastic bodies 96 may extend in the transverse direction to provide a ring like elastic belt 40 when the front belt 84 and the back belt 86 are joined. At least some of the elastic bodies 96 extend in the transverse direction substantially parallel to each other. All of the elastic bodies 96 may extend in the transverse direction substantially parallel to each other. Such an article may be economically made. The front and back belt 84, 86 each may have transversely continuous proximal and distal edges, the proximal edge 90 being located closer than the distal edge 88 relative to the longitudinal center of the article. The elastic bodies 96 may be disposed in the same or different denier, interval, and force between the front and back, as well as in different longitudinal positions of the belt.

Figure 3A:
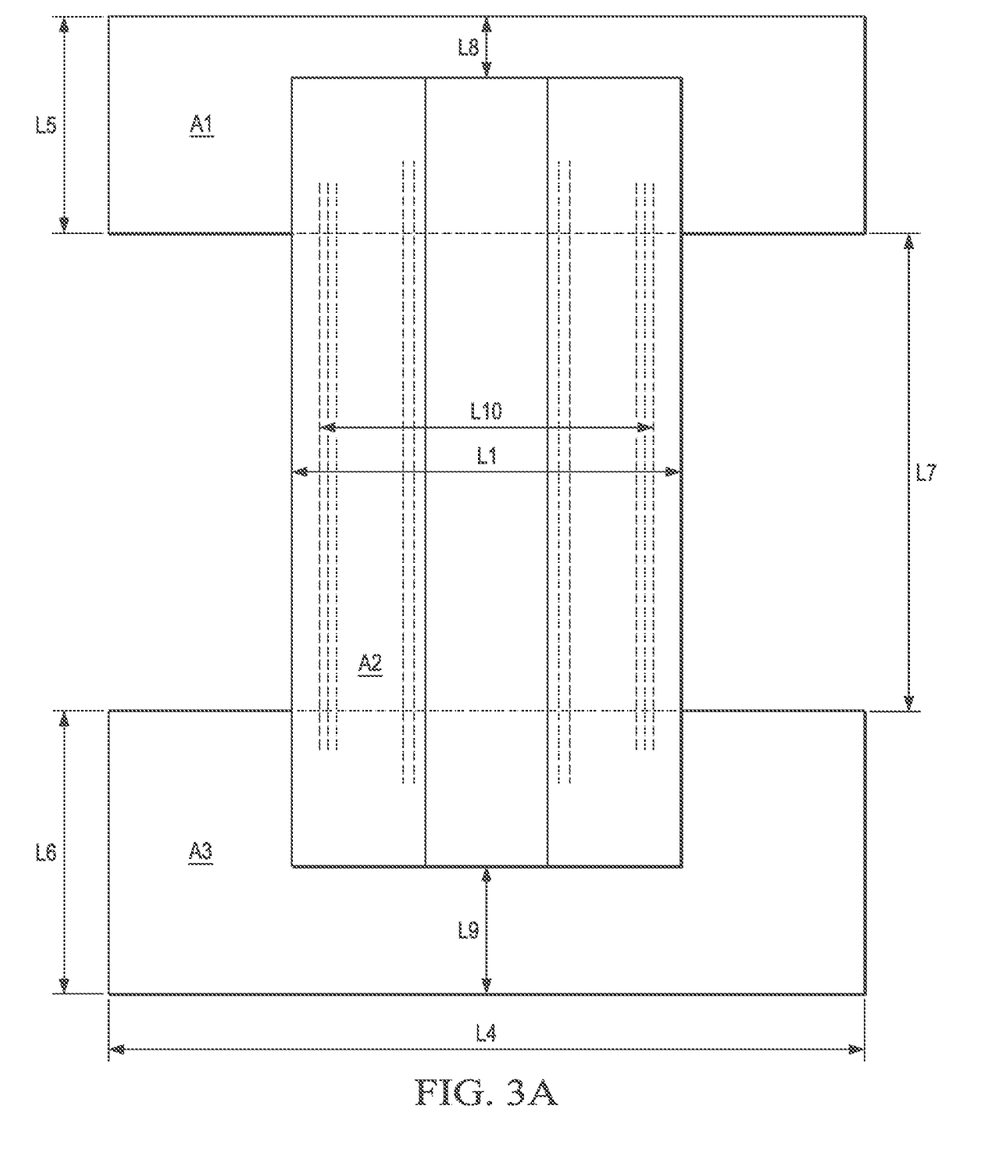
FIG. 3A-3E are schematic plan views of embodiments of wearable articles of the present invention with the seams unjoined and in a flat uncontracted condition showing the body facing surface, indicating certain dimensions according to the "Article Dimension Measurement".
Figure 3B:
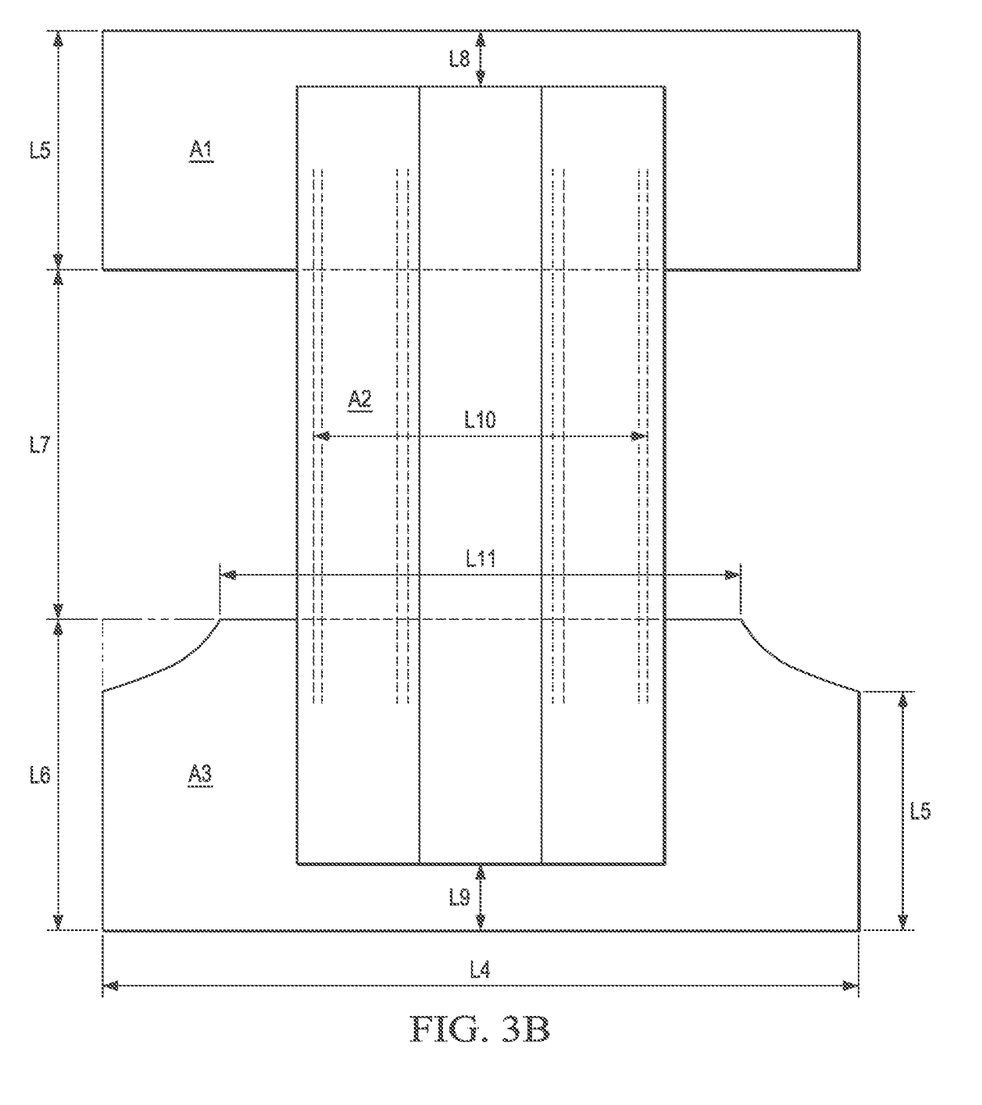
Figure 3C:
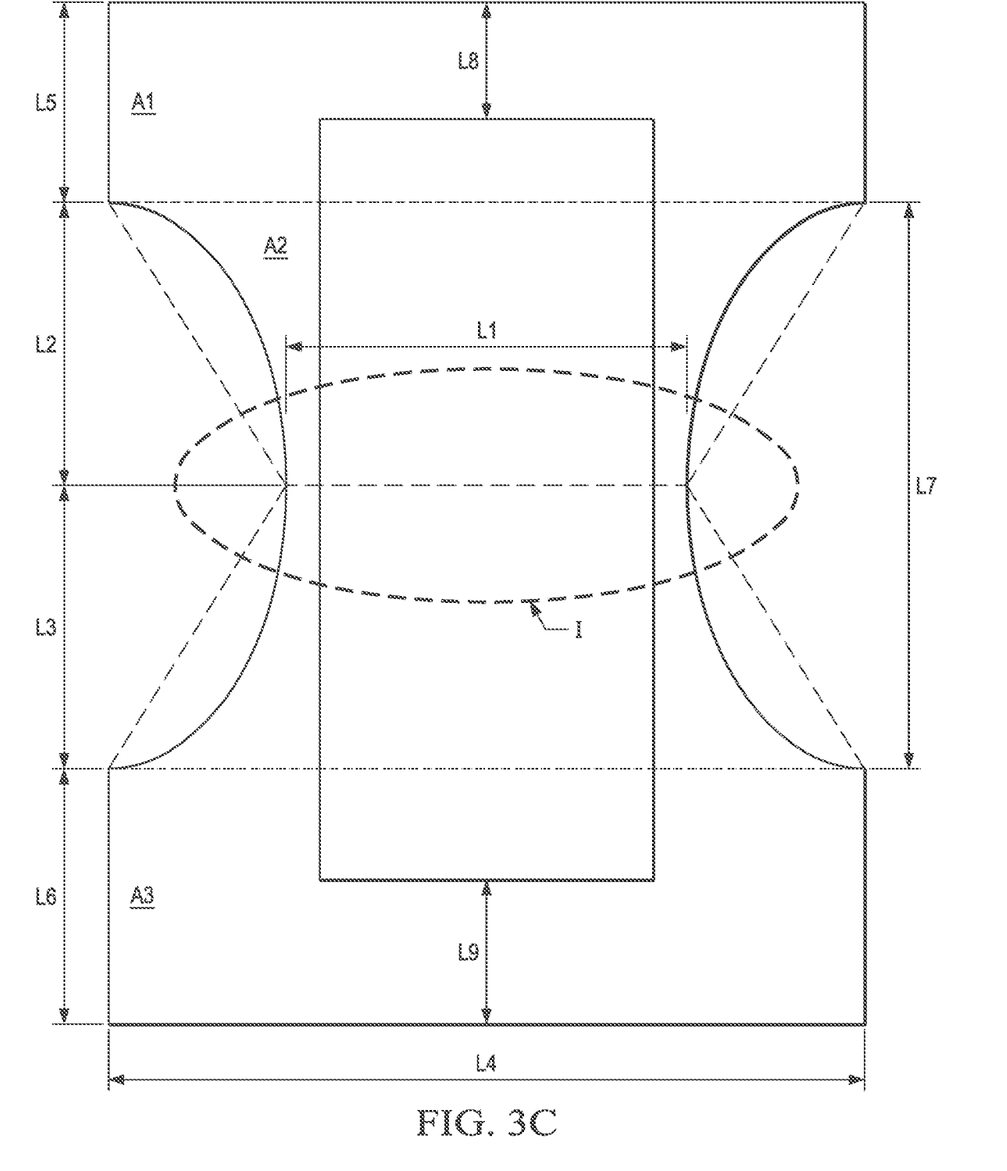

The article of the present invention have dimensions which provide improved fit properties while still being economical to manufacture. FIGS. 3A-3E are schematic plan views of embodiments of wearable articles of the present invention with the seams unjoined and in a flat uncontracted condition showing the body facing surface. In FIGS. 3A-3C, the perimeter of the central chassis is shown in solid line, although they may be covered by a folded over material of the front and/or back elastic belt region.

Referring to FIGS. 3A-3C, the article of the present invention comprises, according to the measurements herein: the front elastic belt region 84 having an area of A1, the crotch region having an area of A2, the back elastic belt region 86 having an area of A3; wherein the total of A1, A2 and A3 is from about 1250 cm$^2$ to about 1400 cm$^2$, and having a relationship of A3>A1>A2. Namely, the area of the back elastic belt region A3 is greater than that of the front elastic belt region A1, and that of the front elastic belt region A1 is greater than that of the crotch region A2, wherein A1+A2+A3 is from about 1250 cm$^2$ to about 1400 cm$^2$. Further, the ratio of A1 to A2 may be from about 1 to about 1.5, and the ratio of A2 to A3 may be less than about 0.7. The article of the present invention comprises, according to the measurements herein: the front elastic belt region 84 having a front placement distance L8, and the back elastic belt region 86 having a back placement distance L9; wherein the ratio of L8 to L9 is no more than about 0.8. Without being bound by theory, the total area of the article A1+A2+A3 is in a relatively low range, yet it is believed there is sufficient coverage for the overall article in the front, crotch, and back regions by providing the back elastic belt region 86 greater than the front elastic belt region 84 and shifting the center chassis 38 toward the front, such that the front region 26 is provided with leakage protection, while the back region 28 is provided with less material to enhance breathability. The article may be a Size 3 or Size 4 baby diaper article.

Depending on geography, these sizes may also be referred to as Size M (Size 3) and Size L (Size 4).

The article of the present invention may have, according to the measurements herein: the transverse length of the crotch region L1 of from about 150 mm to about 210 mm, or from about 180 mm to about 190 mm. Without being bound by theory, it is believed that by providing the transverse length of the crotch region L1 relatively narrow, the fit of the article is improved even after the article carries load. The article of the present invention may have, according to the measurements herein: the front elastic belt region 84 and the back elastic belt region 86 have the same effective belt width L4, wherein the ratio of the transverse length of the crotch region L1 to the effective belt width L4 is no more than about 0.7, or between about 0.49 to about 0.61. Without being bound by theory, it is believed that utilizing material for securing the transverse length of the elastic belt regions is advantageous.

Figure 3D:
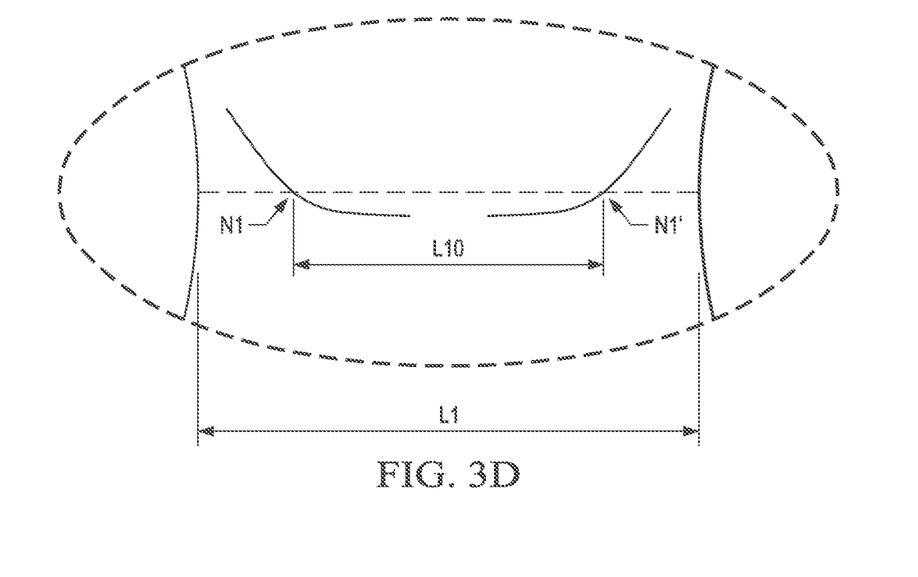
Figure 3E:
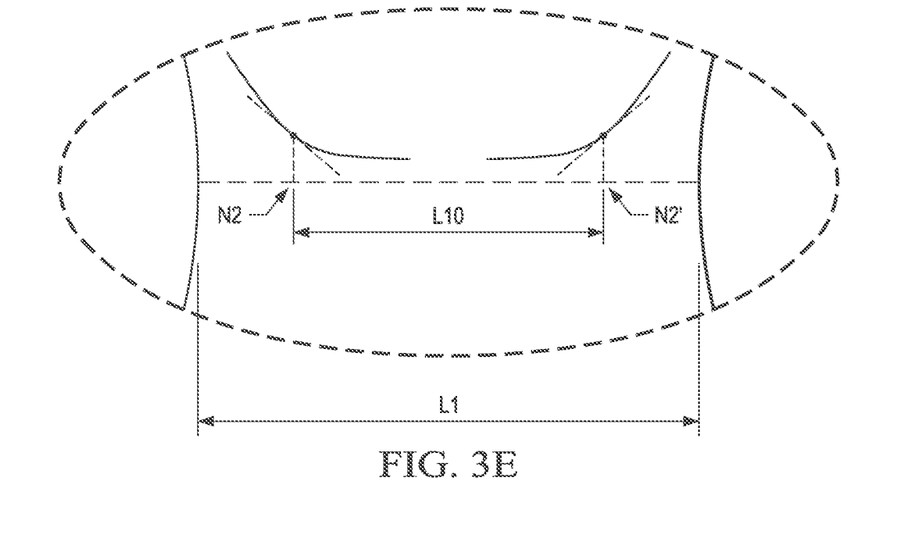

The article of the present invention comprises a central chassis 38 comprising a pair of leg elastics extending at least partially along the longitudinal axis in the crotch region, and have an outer leg elastic spacing L10 of from about 150 mm to about 210 mm, or from about 160 mm to about 190 mm, according to the measurements herein. Referring to FIGS. 3A-3B, the article of the present invention may have a pair of leg elastics disposed along the longitudinal axis, and have an outer leg elastic spacing L10 which may be directly measured. Referring to FIG. 3C, the leg elastics may be disposed along the curved contour of the center chassis 30. For such configuration, L10 is obtained according to FIGS. 3D-3E, which are exploded views of region I of FIG. 3C, wherein the leg cuffs are shown in solid line. Referring to FIGS. 3D-3E, the article of the present invention may have a pair of leg elastics curved inwardly toward the transverse center of the core region. For those articles, the outer leg elastic spacing L10 is assumed according to the measurements detailed below. Without being bound by theory, it is believed that by providing the combination of the selected transverse length of the crotch region L1 and outer leg elastic spacing L10, the fit of the article is improved even after the article carries load.

The front and/or back elastic belt regions 84, 86 may be treated such that certain of the area overlapping the front and/or back waist panel 52, 54 of the central chassis 38 are removed of elasticity. Removal of elasticity from a certain area of the front and/or back waist panel 52, 54 may be advantageous when the central chassis 38 comprises an absorbent core 62, in that elasticity in the front and/or back area overlapping the absorbent core 62 may cause bunching of the absorbent layer or any of the layers in the absorbent core 62 and interfere with close fit of the central chassis 38 to the wearer. At least a portion of, or at least 10% of, or at least 20% of, or at least 30% of, the elasticity of; at least one of, or at least half of, or at least two thirds of, the elastic bodies are removed in the region overlapping with the front and back waist panels 52, 54 of the central chassis 38. The elastic bodies 96 overlapping the absorbent material non-existing region 61 may be disposed in active elasticity for good fit of the central chassis 38. This may be advantageous in preventing leakage. Referring to FIG. 2, the entire area where the elastic bodies 96 overlap with the absorbent core 62 may be removed of its elasticity. Alternatively, the elastic bodies 96 toward the distal edges of the absorbent core 62 may be disposed in active elasticity.

Referring to FIGS. 2 and 3A-3C, the back elastic belt region 86 may have a greater belt length L6 than the front belt length L5 of the front elastic belt region 84 along all of, or part of its effective belt width L4 in the transverse direction. The entirety of the front belt length L5 may be seamed, such that the seam length is the same as the front belt length L5. When the wearable article is assembled to form the waist opening and the leg openings, the wearable article 20 is folded along the transverse centerline TX such that the front distal edge 88 is aligned with the back distal edge 88. The front side edge 89 is also aligned with a portion of the back side edge 89. Then the front elastic belt region 84 and the back elastic belt region 86 are joined at the front and back side edges 89 at the seams 32. Referring to FIG. 3B, the front and back proximal edges 90 may be matched at the side seam 32 by creating a notch for the back belt 86 in the vicinity of the side seam. Referring to FIGS. 3A and 3C, the front and back proximal edges 90 may not be aligned to one another. The back proximal edge 90 may be disposed longitudinally closer than the front proximal edge 90 relative to the transverse center line TX such that the proximal portion of the back side panel 82 extends toward the crotch panel 56 of the central chassis 38 beyond the front proximal edge 90. The side edge of the proximal portion of the back side panel 82 may not be joined to anywhere and free from attachment. Thus, the proximal portion of the back side panel 82 provides a buttock cover 95 as in FIG. 1.

The elastic belt region 40 may be closely associated with the function and quality of the article. Thus, materials for forming the elastic belt region 40, as well as the elastic profile of the elastic belt region, are carefully selected by the manufacturer for providing the desirables for the article. An undergarment kind of appearance and pleasant tactile sense such as flexibility and cushiony touch may be associated with high quality. Ease of stretch and application, while also maintaining certain force during wear to prevent the article from sagging after loading, may be associated with high function. The balance of the aforementioned quality and function attributes provide the favorable entire usage experience of the article by the user. The user may be the wearer or the caregiver.

Figure 4A:
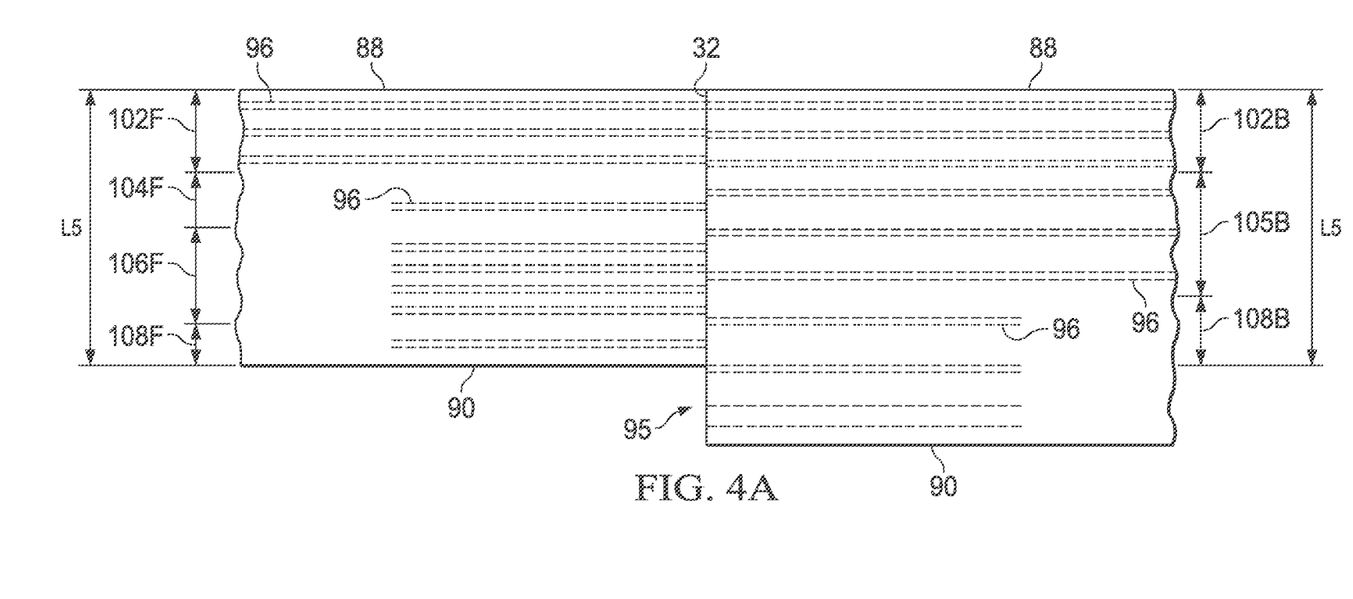
FIGS. 4A and 4B are schematic side plan views of embodiments of wearable articles of the present invention in a flat uncontracted condition showing the garment facing surface.
Figure 4B:
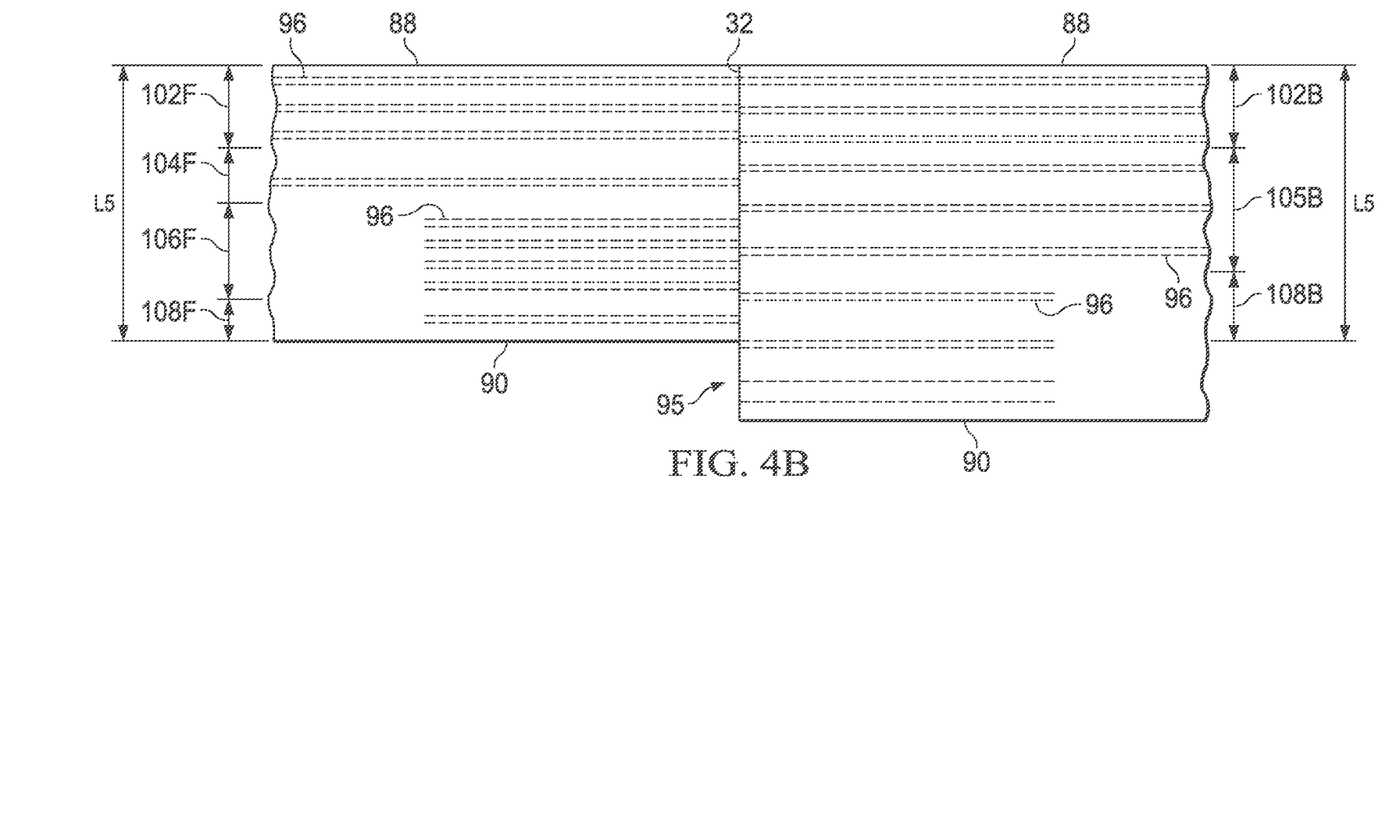

Referring to FIGS. 4A and 4B which are belt-type pants having a contour of FIG. 3A observed from the side seam, the tensile stress (N/m) of the front and back belts 84, 86, respectively, may be profiled in order to provide the benefits of the present invention. The tensile stress may be measured, for example, by the Belt Zone Tensile Stress Measurement described herein below. When the elasticity of the front and back belts 84, 86 are provided by a plurality of elastic bodies 96 running in the transverse direction, the tensile stress may be adjusted by one or more of the following methods; 1) elongation rate of the elastic body 96; 2) density (dtex) of the elastic body 96; 3) longitudinal interval of multiple elastic bodies 96; and 4) effective length of elasticity of the elastic body 96 in the transverse direction. The elastic bodies may be elastic strands having a dtex of from about 470 to about 1100 and disposed at an elongation of from about 110% to about 290%. By elongation, "0% elongation" is meant the original length of the elastic body 96.

Some elastics may be disposed to impart higher tensile stress in certain regions. A plurality of elastics may collectively be disposed to impart a relatively higher or lower tensile stress compared to other regions. When the entirety of the front belt length L5 is seamed, such collective elastics are referred to herein as zones, wherein each zone extends in the transverse direction and defined by its location from the distal edge 88 to the proximal edge 90 relative to the percentage of the front belt length L5 or seam length L5, as such:

|      | Percentage from distal edge | Zone definition |
|------|------|------|
| Front | 0-30% | Waist zone 102F |
|       | 30%-50% | Distal tummy zone 104F |
|       | 50-85% | Proximal tummy zone 106F |
|       | 85-100% | Leg zone 108F |
| Back | 0-30% | Waist zone 102B |
|      | 30%-75% | Tummy zone 105B |
|      | 75%-100% | Leg zone 108B |

Zones of higher tensile stress may be disposed with an array of 2-4 elastic strands having an interval within the array of between 2-4 mm. The tensile stress of the back tummy zone 105B may be higher than the tensile stress of any other zone. The tensile stress of the front proximal tummy zone 106F may be higher than the tensile stress of any other zone on the front, or no less than about 200% of the tensile stress of the front distal tummy zone 104F. The array may be disposed on the back tummy zone 105B. The array may be disposed on the front proximal tummy zone 106F.

The article of the present invention may have a suitable Stretch Circumference Force (N) according to the Whole Article Force Measurement below. What is meant by Stretch Circumference Force is the loading force at a certain stretch level which is believed to simulate initial stretch experience felt by the user when inserting hands and stretch opening the article. The level of stretch which is believed to be felt by the user when stretch opening the article is represented by the "470 mm Stretch Circumference". The dimension of 470 mm is selected based on a study by the Applicant whereby the average standing hip circumference (mm) at the height matching the pubic bone of children having a body weight of 6-20 kg was 473 mm based on data from over 1000 subjects. Namely, according to common habits for wearing a pant article, the user would stretch open the elastic belt region of the pant article to a circumference more or less matching that of the hip circumference of the body of the wearer. A body weight of 6-20 kg matches the recommended body weight of wearers for pant articles of Sizes 3-6 (Sizes M to XXL). The article of the present invention has a Stretch Circumference Force of no greater than about 7N, or no greater than about 6.5N, or no greater than about 6N. By having such Stretch Circumference Force, the elastic belt can be easily opened and applied. Without being bound by theory, it is believed that the lower the Stretch Circumference Force, the elastic belt region may be stretched with less force, thus softer the perception of the elastic belt region by the user.

The article of the present invention may have a suitable Fit Circumference Force (N) according to the Whole Article Force Measurement below. What is meant by Fit Circumference Force is the unloading force at a certain stretch level which is believed to simulate the force felt by the wearer while wearing the article. The level of stretch which is believed to be felt by the wearer while wearing the article is also represented by the 470 mm Stretch Circumference. The article of the present invention has a Fit Circumference Force of no less than about 2N. By having such Fit Circumference Force, the elastic belt provides good fit to prevent sagging and leakage.

Without being bound by theory, it is believed that by having a relatively low Stretch Circumference Force of no greater than about 7N in combination with a minimum Fit Circumference Force of no less than about 2N, an elastic belt region having ease of application and a secure yet soft fit may be provided. Without being bound by theory, it is believed that by providing the aforementioned Stretch Circumference Force and Fit Circumference Force, the pant-type article of the present invention provides an overall satisfactory tactile sense to the user upon touching, applying, and wearing the article.

1. Whole Article Force Measurement

Force of a pant-type article is measured using an Electronic Tensile Tester with a computer interface such as the MTS Criterion C42 running TestWorks 4 Software (available from MTS SYSTEMS (CHINA) CO., LTD) or equivalent instrument. A load cell is selected so that force results for the samples tested will be between 10 and 90% of capacity of the load cell used. The instrument is calibrated according to the manufacturer's instructions. All testing is performed in a room maintained at 23±2° C. and 50±5% relative humidity.

Figure 5:
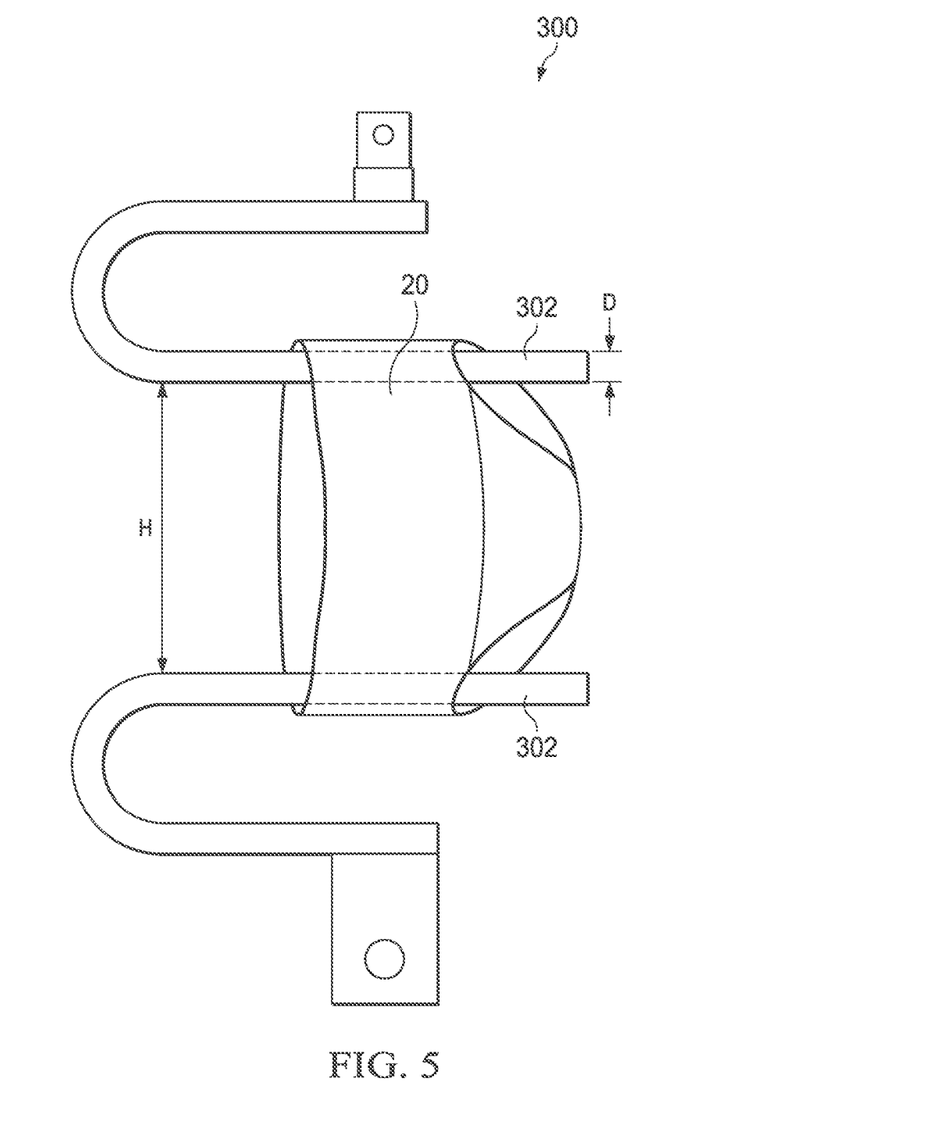
FIG. 5 is a schematic view of an example of a hanger-type sample holding fixture according to the "Whole Article Force Measurement".

The tensile tester is fitted with hanger-type sample holding fixtures 300 as shown in FIG. 5. Each fixture comprises a rigid linear rubber-coated horizontal bar section 302 to prevent sample slippage during testing. The outer bar diameter (including the rubber coating) of the horizontal bar sections is 10.0 mm. The central axes of the horizontal bar sections 302 are configured to remain parallel and in the same vertical plane throughout the test procedure. The gauge circumference is determined by the following equation:

Gauge Circumference=2×(H+D+πD/2)

where H is the vertical gap between the horizontal bar sections 302, and D is the outer diameter of the bar.

The instrument is set up to go through the following steps:

| | |
|---|---|
| Crosshead Speed | 254.0 mm/min |
| Final Load Point | 19.6N |
| Hold Time | 0 |
| Number of Cycles | 1 |
| Data Acquisition Rate | 50 Hz |

A sample article 20 is inserted onto the upper horizontal bar section 302 so that the bar passes through the waist opening and one leg opening of the article. The crosshead is raised until the specimen hangs above the lower bar and does not touch lower bar 302. The load cell is tared and the crosshead is lowered to enable the lower bar 302 to be inserted through the waist opening and other leg opening without stretching the article. The article is adjusted so that the longitudinal centerline LX of the article is in a horizontal plane halfway between the upper and lower bars 302. The center of the side portion in contact with the bar 302 is situated on the same vertical axis as the instrument load cell. The crosshead is raised slowly while the article is held in place by hand as necessary until the force is between 0.05 and 0.1N, while taking care not to add any unnecessary force. The gauge circumference at this point is the Initial Gauge Circumference. The test is initiated and the crosshead moves up at 254 mm/min until a force of 30N is attained, then the crosshead immediately returns to the Initial Gauge Circumference at the same speed. The circumference at 19.6N and the circumference at 30N during the extension segment of the test are recorded.

The circumference at 19.6N is defined as the 19.6N Circumference (mm), and the circumference at 30N is defined as the 30N Circumference (mm). The Stretch Circumference Force is defined as the force at 470 mm Stretch Circumference during the load (extension) segment of the test. The Fit Circumference Force is defined as the force at 470 mm Stretch Circumference during the unload (contraction) segment of the test.

Five samples are analyzed and their average Initial Gauge Circumference, average 19.6 Circumference, average 30N Circumference, average Stretch Circumference Force and average Fit Circumference Force are calculated and reported to the nearest 1 mm or 0.01 N, respectively.

2. Article Dimension Measurement

To obtain a sample for this measurement, the side seams 32 of an article are opened, and the body-facing side of the entire article is attached on surface of a non-transparent backboard by hook material, or double side tape material. The backboard should be large enough to support the entire area of the article. When attaching, any elastics are stretched to its "maximum stretched state" wherein the following conditions a)-c) are met, unless any material failure is observed.

a) The side seams are straight.
b) There are no wrinkles on the central chassis or the belt elastic regions.
c) The left part and right part of the article in view of the longitudinal axis LX are symmetrical.

For most articles, the front and back elastic belt regions may be stretched up to the "30N Circumference" as measured under the "Whole Article Force Measurement" above, for meeting the conditions above. In case any material failure is observed prior to reaching a level of stretch wherein the above conditions are met, then the point of maximum stretch at which the material is yet to fail is considered the "maximum stretched state". Material failure may include decomposing of nonwoven material, breaking of elastic strands, or the like.

What is measured is the following dimensions of the sample, wherein some of the dimensions are measured differently depending on the contour of the article. FIGS. 3A-3C are representative article contours for explaining how the dimensions are measured, and not intended to be an exhaustive list of article contours of the present invention. For example, the article may take a belt region contour of FIG. 3B and a crotch region contour of FIG. 3C. Although the body-facing side of the sample is attached to the backboard and thus not seen, FIGS. 3A-3C describe the body-facing side in order to explain the dimensions below.

The dimensions are reported to the nearest 1 mm. Five samples are measured and their average are obtained.

L1: transverse length of crotch region; is the minimum transverse length of the crotch region as shown in FIGS. 3A-3C.

L2: longitudinal length of front crotch region; is the longitudinal length between an imaginary line drawn for obtaining L1 (hereinafter "crotch phantom line") and the proximal edge of the front elastic belt region, as in FIG. 3C.

L3: longitudinal length of back crotch region; is the longitudinal length between the crotch phantom line and the proximal edge of the back elastic belt region, as in FIG. 3C.

L4: effective belt width; is the maximum transverse width of the back elastic belt region, as in FIGS. 3A-3C.

L5: front belt length; is the maximum longitudinal length of the front elastic belt region, as in FIGS. 3A-3C. When the entirety of the front belt length is seamed, L5 may also be referred to as the seam length.

L6: back belt length; is the maximum longitudinal length of the back elastic belt region, as in FIGS. 3A-3C.

L7: longitudinal length of crotch region; is the longitudinal length between the proximal edge of the front elastic belt region and the proximal edge of the back elastic belt region, as in FIGS. 3A and 3C. In FIG. 3C, L7 equals the sum of L2 and L3.

L8: front placement distance; is the longitudinal length between the front waist opening and the front distal edge of the central chassis, as in FIGS. 3A-3C.

L9: back placement distance; is the longitudinal length between the back waist opening and the back distal edge of the central chassis, as in FIGS. 3A-3C.

L10: outer leg elastic spacing; is the transverse length between the outermost leg elastics placed on the crotch phantom line. For articles having longitudinally extending leg elastics as in FIGS. 3A and 3B, L10 may be measured anywhere in the crotch region. For articles having leg elastics which are curved acutely in the crotch region, the transverse length between the intersections N1 and N1' of the outermost leg elastics and the crotch phantom line are measured, as in FIG. 3D. For articles having leg elastics which are curved acutely in the crotch region and wherein the outermost leg elastics and the crotch phantom line do not intersect, an imagery tangent line is drawn from the most convex portion of the leg elastics, then a perpendicular line is drawn from the tangency point against the crotch phantom line as in FIG. 3E, and the transverse length between the imaginary intersections N2 and N2' are measured.

L11: minimum belt width; is the minimum transverse width of the back elastic belt region, as in FIG. 3B. Although not described, such minimum belt width L11 may also exist on the front elastic belt region.

A3: back elastic belt region area is obtained by the following formula: L4×L6 when the back elastic belt region area is rectangular as in FIGS. 3A and 3C. For a back elastic belt region taking a contour as in FIG. 3B, the area is obtained by subtracting the approximate removed area, namely obtained by the following formula: L4×L6−(L4−L11)×(L6−L5).

A2: crotch region area; is obtained by the following formula: L1×L7 when the center chassis is rectangular as in FIGS. 3A and 3B. For a crotch region area which is not rectangular as in FIG. 3C, the area is obtained by assuming the approximate area, namely the following formula: (L2+L3)×(L4+L1)÷2.

A1: front elastic belt region area; is obtained by the following formula: L4×L5 when the front elastic belt region area is rectangular as in FIGS. 3A-3C. For a front elastic belt region taking a contour similar to the back elastic belt region of FIG. 3B, the area is obtained by subtracting the approximate removed area in a similar manner as explained above for A3.

3. Belt Zone Tensile Stress Measurement

The Zone Tensile Stress Measurement herein is for articles wherein the front belt and the back belt form a ring-like elastic belt, and all of the elastic bodies sandwiched between the inner sheet and the outer sheet run in the transverse direction substantially parallel to each other.

The tensile stress (N/m) is calculated by tensile force (N) divided by the longitudinal length (m) of the specimen. Force may be measured using an Electronic Tensile Tester with a computer interface such as the MTS Criterion C42 running TestWorks 4 Software (available from MTS SYSTEMS (CHINA) CO., LTD) or equivalent instrument. A load cell is chosen so that force results for the samples tested will be between 10 and 90% of capacity of the load cell. The instrument is calibrated according to the manufacturer's instructions. All testing is performed in a room maintained at 23±2° C. and 50±5% relative humidity. The instrument is equipped with single line contact grips at least as wide as the test specimen.

To obtain test specimens, the sample article is opened at both side seams in a manner such that the front and back belts are peeled away from each other without removing the side seam area, and the front and rear elastic belts are removed from the central chassis 38 by separating the bonding between the waist belt and central chassis. Cold spray may be used, paying attention not to make wrinkles in the belt sections. Care is taken not to spray on any belt elastic body 96. The obtained front and back belts 84, 86 are severed into zones 102F, 104F, 106F, 108F, 102B, 105B, and 108B as defined above with care not to cut any elastic body 96. Samples are pre-conditioned at 23±2 C.° and 50±5% relative humidity for two hours prior to testing. Measure the longitudinal length of each specimen by a generic metal ruler to the nearest 1 mm. By longitudinal length, what is meant is the dimensions 102F, 104F, 106F, 108F, 102B, 105B, and 108B in FIGS. 4A and 4B.

The instrument is set up to go through the following steps. Initial Gauge Length is calculated from the Initial Gauge Circumference which is determined during the Whole Article Force Test using separate identical articles, as described above. The Initial Gauge Length is defined as 50% of the Initial Gauge Circumference. The Final Gauge Length is calculated from the 19.6N Circumference which is determined during the Whole Article Force Test, as described above.

| | |
|---|---|
| Crosshead Speed | 254.0 mm/min |
| Data Acquisition Rate | 50 Hz |
| Final Gauge Length | 0.5 × 19.6N Circumference |
| Hold Time | 0 |
| Number of Cycles | 1 |

One end of the specimen is clamped into the upper clamp using the side seam area and the load is tared. The other end of the specimen is clamped into the lower clamp also using the side seam area, such that only the side seam areas are behind the contact line of the grip. The test is started and the specimen is extended to the Final Gauge Length at a crosshead speed of 254 mm/min, then immediately returned to the Initial Gauge Length at the same speed. The specimen is extended in the article transverse direction during the test. The unload force at 70% of the Final Gauge Length during the unload segments of the test is recorded.

Five articles are analyzed and the unload forces are recorded for each of the front and back zones 102F, 104F, 106F, 108F, 102B, 105B, and 108B. The average tensile force (N) is calculated to the nearest 0.01 N for each zone including the front and back specimens for that zone. The tensile stress for each zone is calculated by the average tensile force (N) divided by the average longitudinal length (m) and reported to the nearest 0.1 N/m.

EXAMPLES

Examples 1-2 and A-C are obtained as such, and subject to measurements as described above.

Example 1: Size 4 (L-size) belt-type pant article having the configuration of FIG. 4A and elastic profile in Table 1 below.

Example 2: Size 4 (L-size) belt-type pant article having the configuration of FIG. 4B and elastic profile in Table 1 below.

Example A: Size 4 (L-size) belt-type pant article sold by the tradename of "Pampers Pants L size imported from Japan" with lot No.634120220020161206 purchased in the China market in 2016 and internal production with number #7519_942 manufactured in July 2017 in Germany.

Example B: Size 4 (L-size) belt-type pant article sold by the tradename of "Mammy Poko Extra Absorb New Crisscross" with Lot No. G16-A45598-006 purchased in India market in 2016.

Example C: Size 4 (L-size) belt-type pant article sold by the tradename of "Mammy Poko Fashion Boy Pants" with Lot No. 20170204D2653 purchased in China market in 2016.

Example D: Size 4 (L-size) belt-type pant article having the same dimension and elastic profile as Example A while using material of lower gsm for the outer sheet, inner sheet, and outer cover layer, internally produced with number #7519_942 manufactured in June 2017 in Germany.

TABLE 1

| | | Example 1 | Example 2 |
|---|---|---|---|
| | | dtex/elongation %/number of elastic bodies | |
| Front | Waist zone | 540dtex/160%/6 | 540dtex/170%/6 |
| | Distal tummy zone | 540dtex/160%/2 | 540dtex/170%/2 |
| | | 540dtex/160%/2 tummy cut | 540dtex/170%/2 |
| | Proximal tummy zone | 940dtex/210%/8 tummy cut | 940dtex/275%/8 tummy cut |
| | Leg zone | 540dtex/160%/2 tummy cut | 540dtex/160%/2 tummy cut |
| Back | Waist zone | 540dtex/160%/6 | 540dtex/160%/6 |
| | Tummy zone | 940dtex/130%/6 | 940dtex/130%/6 |
| | Leg zone | 540dtex/210%/6 tummy cut | 540dtex/210%/6 tummy cut |

(*1) tummy cut in Table 1 refers to removal of elasticity at the central area of elastic strands which overlap the central chassis, resulting in 66% effective length of elasticity.

The article dimensions were measured according to the Article Dimensions Measurement methods herein, wherein Examples 1-2 and A were measured according to FIG. 3A, and Examples B and C were measured according to FIG. 3B. For Examples 1-2 and A-C the force parameters according to the Whole Article Force Measurement herein were measured. Results are found in Table 2.

TABLE 2

| | Example 1 | Example 2 | Example A | Example B | Example C |
|---|---|---|---|---|---|
| Effective belt width L4 (mm) | 355 | 355 | 355 | 326 | 360 |
| Back minimum belt width L11 (mm) | NA | NA | NA | 195 | 220 |
| Front belt length L5 (mm) | 121 | 116 | 126 | 120 | 117 |
| Back belt length L6 (mm) | 156 | 151 | 161 | 120 | 117 |
| Transverse length of crotch region L1 (mm) | 190 | 190 | 206 | 166 | 167 |
| Longitudinal length of crotch region L7 (mm) | 193 | 193 | 193 | 168 | 185 |
| Front placement distance L8 (mm) | 16 | 27 | 16 | 28 | 29 |
| Back placement distance L9 (mm) | 51 | 63 | 24 | 72 | 27 |

TABLE 2-continued

|  | Example 1 | Example 2 | Example A | Example B | Example C |
|---|---|---|---|---|---|
| Outer leg elastic spacing L10 (mm) | 166 | 166 | 178 | 171 | 167 |
| Front elastic belt region area A1 (mm$^2$) | 430 | 412 | 447 | 391 | 421 |
| Crotch region area A2 (mm$^2$) | 367 | 367 | 398 | 302 | 315 |
| Back elastic belt region area A3 (mm$^2$) | 554 | 536 | 572 | 511 | 566 |
| Total of A1 + A2 + A3 (mm$^2$) | 1350 | 1315 | 1416 | 1205 | 1302 |
| Ratio L8/L9 | 0.31 | 0.43 | 0.67 | 0.39 | 1.07 |
| Ratio A1/A2 | 1.2 | 1.1 | 1.1 | 1.3 | 1.9 |
| Ratio A2/A3 | 0.66 | 0.68 | 0.70 | 0.59 | 0.25 |
| Ratio L1/L4 | 0.54 | 0.54 | 0.58 | 0.52 | 0.47 |
| Fit Circumference Force (N) | 3.08 | 3.12 | 3.67 | 2.99 | 2.67 |

The articles of Examples 1 and 2 of the present invention provide overall good fit, underwear like appearance, good fit at the legs, and good breathability.

Consumer Acceptance Test

Test 1

53 panelists who were caregivers of babies using Size 4 pant diapers at a frequency of at least 3 pants/week, and willing to use 1 pant/day and 1 pant/night during the test period, and having a mixture of usage experience of major brands were recruited. There were about equal number of caregivers of boy and girl babies. Each panelist was given one product first with a 5 days usage and then another product with another 5 days usage. Roughly half of the panelists were given Example 2 first, and the other half were given Example D first. After finishing usage of 2 products, each panelist was asked which product was better overall, or if they had no preference. The rating of 53 panelists are reported in percentage in Table 3.

TABLE 3

| Values/Questions | Example 2 | Example D | No preference |
|---|---|---|---|
| Overall product preference (%) | 49 (*1) | 28 | 23 |

(*1) Statistically significant compared to Example D at a risk of 90%

Test 2

30 panelists who were caregivers of babies using Size 4 pant diapers and having a mixture of usage experience of major brands were recruited. There were about equal number of caregivers of boy and girl babies. Each panelist was given one product first with a 5 days usage and then another product with another 5 days usage. Roughly half of the panelists were given Example 1 first, and the other half were given Example A first. After finishing usage of 2 products, each panelist was asked which product was better in terms of overall fit, or if they had no preference. The rating of 30 panelists are reported in percentage in Table 4.

TABLE 4

| Values/Questions | Example 1 | Example A | No preference |
|---|---|---|---|
| Preference overall fit (%) | 20 | 13 | 67 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Further, every numerical range given throughout this specification includes every narrower numerical range that falls within such broader numerical range.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wearable article continuous in a longitudinal direction and a transverse direction comprising a front elastic belt region, a back elastic belt region, a crotch region, a waist opening and two leg openings; the crotch region extending longitudinally between the front elastic belt region and the back elastic belt region;

the front elastic belt region having an area of A1, the crotch region having an area of A2, the back elastic belt region having an area of A3, the front elastic belt region having a front placement distance L8, and the back elastic belt region having a back placement distance L9 according to the measurements herein;

wherein the total of A1, A2 and A3 is from about 1250 cm$^2$ to about 1400 cm$^2$, and having a relationship of A3>A1>A2; and wherein the ratio of L8 to L9 is no more than about 0.8;

wherein the article is formed of a center chassis and a ring-like elastic belt comprising the front elastic belt region and the back elastic belt region; the center of the front elastic belt region is joined to a front waist panel of the center chassis, the center of the back elastic belt region is joined to a back waist panel of the center chassis, the front and back elastic belt regions each having a left side panel and a right side panel where the central chassis does not overlap, wherein the front and back elastic regions each are a laminate of an inner sheet, an outer sheet, and a plurality of elastic strands sandwiched therebetween, wherein all of the elastic strands sandwiched between the inner sheet and the outer sheet run in the transverse direction substantially parallel to each other;

the entirety of the length of the belt side edge of the front elastic belt region is seamed with a certain length of the belt side edge of the back elastic belt region to define a seam length L5;

the front belt region divided into 4 zones extending in the transverse direction and defined by its location from the distal edge to the proximal edge relative to the percentage of the seam length L5 wherein; 0-30% is a waist zone, 30-50% is a distal tummy zone, 50-85% is a proximal tummy zone, and 85-100% is a leg zone;

the back elastic belt region divided into 3 zones extending in the transverse direction and defined by its location from the distal edge to the proximal edge relative to the percentage of the seam length L5 wherein; 0-30% is a waist zone, 30-75% is a tummy zone, and 75-100% is a leg zone; and wherein the tensile stress of the back tummy zone is higher than the tensile stress of any other zone.

2. The article of claim 1, wherein the ratio of A1 to A2 is from about 1 to about 1.5, and the ratio of A2 to A3 is less than about 0.7.

3. The article of claim 1, wherein the transverse length of the crotch region L1 is from about 150 mm to about 210 mm according to the measurements herein.

4. The article of claim 3, wherein the front elastic belt region and the back elastic belt region have the same effective belt width L4, wherein the ratio of the transverse length of the crotch region L1 to the effective belt width L4 is no more than about 0.7 according to the measurements herein.

5. The article of claim 3, wherein the crotch region comprises a pair of leg elastics extending at least partially along the longitudinal axis in the crotch region, and have an outer leg elastic spacing L10 of from about 150 mm to about 210mm according to the measurements herein.

6. The article of claim 1, wherein the article has a Fit Circumference Force of no less than about 2N according to the measurements herein.

7. The article of claim 1, wherein the crotch region comprises a topsheet, a backsheet and an absorbent core positioned between the topsheet and the backsheet, the absorbent core further comprising an absorbent layer and an acquisition layer, wherein the absorbent layer is substantially cellulose free.

8. The article of claim 7, wherein the absorbent layer comprises a longitudinally extending channel, the channel being substantially free of absorbent material.

9. The article of claim 8, wherein a channel is further formed in the acquisition layer, wherein the channel of the acquisition layer at least partially matches the channel of the absorbent layer in the thickness direction.

10. The article of claim 1, wherein the article is a Size 3 or Size 4 baby diaper article.

* * * * *